US 7,487,774 B2

(12) United States Patent
Acker

(10) Patent No.: US 7,487,774 B2
(45) Date of Patent: Feb. 10, 2009

(54) ADAPTIVE PATIENT TRIGGER THRESHOLD DETECTION

(75) Inventor: Jaron M. Acker, Madison, WI (US)

(73) Assignee: The General Electric Company, Schenectady, NY (US)

( * ) Notice: Subject to any disclaimer, the term of this patent is extended or adjusted under 35 U.S.C. 154(b) by 559 days.

(21) Appl. No.: 11/197,838

(22) Filed: Aug. 5, 2005

(65) Prior Publication Data

US 2007/0028920 A1    Feb. 8, 2007

(51) Int. Cl.
*A61M 16/00*    (2006.01)
(52) U.S. Cl. ............................ 128/204.18; 128/204.21; 128/204.22; 128/204.23; 128/204.26; 128/205.11; 128/200.24
(58) Field of Classification Search ............ 128/204.21, 128/200.24, 204.18, 204.22, 204.23, 204.26, 128/905, 920
See application file for complete search history.

(56) References Cited

U.S. PATENT DOCUMENTS

| 5,647,351 | A  | * | 7/1997  | Weismann et al. | ..... | 128/204.21 |
| 6,148,814 | A  | * | 11/2000 | Clemmer et al.  | ....... | 128/200.24 |
| 6,484,719 | B1 | * | 11/2002 | Berthon-Jones   | ........ | 128/204.23 |
| 6,626,175 | B2 |   | 9/2003  | Jafari et al.   | ............ | 128/204.21 |
| 7,000,612 | B2 | * | 2/2006  | Jafari et al.   | ............ | 128/204.21 |
| 7,055,522 | B2 | * | 6/2006  | Berthon-Jones   | ........ | 128/204.18 |
| 2003/0188748 | A1 | * | 10/2003 | Sinderby et al. | ....... | 128/204.21 |
| 2003/0213489 | A1 | * | 11/2003 | Mechlenburg et al. | . | 128/204.18 |
| 2004/0040560 | A1 | * | 3/2004  | Euliano et al.  | ......... | 128/204.23 |
| 2007/0163590 | A1 | * | 7/2007  | Bassin          | .................... | 128/204.23 |

OTHER PUBLICATIONS

Chatburn, Computer Control of Mechanical Ventilation, May 2004, Respiratory Care, vol. 49, No. 5, pp. 507-517.*

* cited by examiner

*Primary Examiner*—Justine R Yu
*Assistant Examiner*—Clinton Ostrup
(74) *Attorney, Agent, or Firm*—Andrus, Sceales, Starke & Sawall, LLP

(57) ABSTRACT

The present invention is a method and system for adaptively detecting a patient trigger threshold. The system and method uses fuzzy-logic control algorithm to detect an appropriate trigger threshold by monitoring the number of patient triggers within a predetermined time frame. The system and method also detects an appropriated trigger threshold by monitoring the complete absence of false triggers over a predetermined time frame, increases in average flow, increases in pressure differential, and pressure drop, in order to lower the trigger threshold. The method and system of the present invention is selectable to the user, and adaptively changes the inspiratory trigger threshold.

8 Claims, 2 Drawing Sheets

ADAPTIVE PATIENT TRIGGER THRESHOLD DETECTION

FIELD OF THE INVENTION

This invention relates to the field of patient respiratory care. More particularly, the invention relates to the field of ventilator trigger sensitivity.

BACKGROUND OF THE INVENTION

Patient ventilators have certain modes that accommodate spontaneous, patient initiated breathing. When using these spontaneous modes, the clinician must select a threshold value for the type of trigger they have selected. This trigger threshold is compared to a flow or pressure value for example, to determine whether a patient is trying to start a breath on his or her own. Periodically the trigger level needs to be adjusted due to sensor drift, performance of procedure, changes in patient conditions, etc.

Current systems, such as those disclosed in U.S. Pat. No. 6,626,175 to Jafari et al (hereinafter Jafari), do not adaptively change the inspiratory trigger threshold and the expiratory threshold. Rather, only the expiratory threshold. Furthermore, current systems do not use standard pressure or flow triggers, and do not automatically adjust the trigger to the most sensitive level. Current systems also do not make these features selectable to the user.

SUMMARY OF THE INVENTION

The present invention is a method and system for adaptively detecting a patient trigger threshold. The system and method detects an appropriate trigger threshold using a fuzzy-logic algorithm that monitors the number of patient triggers within a predetermined time frame. The system and method also detects an appropriated trigger threshold by monitoring the complete absence of false triggers over a predetermined time frame, increases in average flow, increases in pressure differential, and pressure drop, in order to lower the trigger threshold. The method and system of the present invention is selectable to the user, and adaptively changes the inspiratory trigger threshold.

A method of adjusting a trigger threshold level of a patient ventilator comprising selecting an auto position on a trigger menu of the patient ventilator, receiving a set of unprocessed data into a sensor, calculating a set of patient data, calculating a control signal with the set of patient data, wherein the control signal reflects the trigger threshold level, and adjusting the trigger threshold level of the patient ventilator with the set of patient data. The method wherein the set of unprocessed data includes an expiratory flow component and an inspiratory flow component, wherein the set of unprocessed data is received by the sensor in a processor, and further wherein the processor calculates the set of patient data and the control signal. The method further comprising sending the set of patient data from the signal processing algorithm processor to a fuzzy logic control algorithm, wherein the fuzzy logic control algorithm executes the adjusting step with the set of patient data and further comprising displaying the set of patient data on a display device coupled to the patient ventilator. The method wherein the adjusting step adjusts the trigger threshold level to a finer level than can be achieved by a manual user interface and further comprising specifying a band wherein the auto position controls within the patient ventilator.

A system for adjusting a trigger threshold level of a patient ventilator comprising a trigger menu of the patient ventilator, wherein the trigger menu is set to an auto position, a sensor configured to receive a set of unprocessed data, a processor, coupled to the sensor, wherein the processor calculates a set of patient data with the set of unprocessed data, and further calculates a control signal with the set of patient data, and further wherein the control signal reflects the trigger threshold level, and a controller coupled to the processor and configured to receive the set of patient data, wherein the controller adjusts the trigger threshold level of the patient ventilator with the set of patient data. The system wherein the set of unprocessed data includes an expiratory flow component, an inspiratory flow component, and a pressure component. The system further comprising a display coupled to the patient ventilator, wherein the display is configured to display the set of unprocessed data and the set of patient data and wherein the processor applies an algorithm to calculate the control signal.

A method of adjusting a trigger threshold of a patient ventilator comprising selecting an auto position on a trigger menu of the patient ventilator, receiving a set of unprocessed data into a sensor, calculating a set of patient data, calculating a control signal with the set of patient data, wherein the control signal reflects the trigger threshold level, sending the control signal from the processor to a controller, adjusting the trigger threshold level of the patient ventilator with the set of patient data, and displaying the set of patient data and the set of unprocessed data on a device coupled to the patient ventilator, wherein the set of unprocessed data includes an inspiratory flow component, an expiratory flow component and a pressure component.

DETAILED DESCRIPTION OF THE INVENTION

Figure 1:
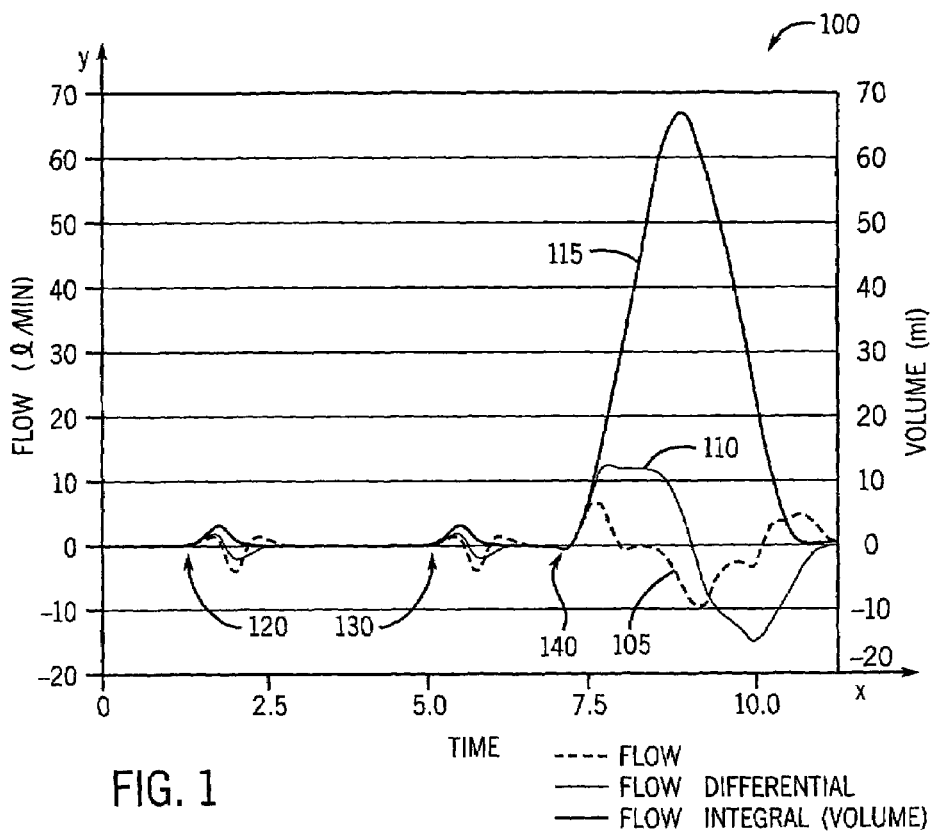
FIG. 1 illustrates a graphical representation of trigger characterization according to an embodiment of the present invention.

FIG. 1 depicts trigger characteristics 100 when the present invention is implemented. The graphical representation of trigger characteristics 100 includes a measure of amplitude in flow (liters per minute) and in volume (mL) along the y axis over a period of time in seconds along the x axis. The trigger characteristics 100 graphical representation of FIG. 1 includes graphical depictions for the flow response 105, flow differential response 110 and volume response 115. A first false trigger 120 and a second false trigger 130, precede the patient trigger 140, which will be discussed below.

Still referring to FIG. 1, the two very short pressure support breaths, the first false trigger 120 and the second false trigger 130, are initiated by auto-triggers followed by a breath caused by a patient trigger 140. Note how the times in which the flow response 105 is elevated are very short in the two false triggers 120, 130 that are auto triggered. In addition, flow differential response 110 times, as well as the volumes response 115 times are very small. Looking at the volume response 115 waveform which takes into account volume in the breathing circuit, it is obvious that a disturbance occurred and the trigger sensitivity should be decreased the next breath. This is because the patient is not actually drawing the gas into his/her lungs. The majority of the gas is flowing back out of the breathing circuit by passing the patient to correct for the disturbance rather than into the patient's lungs.

Still referring to FIG. 1, very short inspirations, exhalations, triggers that result in extremely small volume responses 115 delivered to the patient, such as the first false trigger 120 and the second false trigger 130, are just some of the ways to detect that the trigger level needs to be raised.

Figure 2:
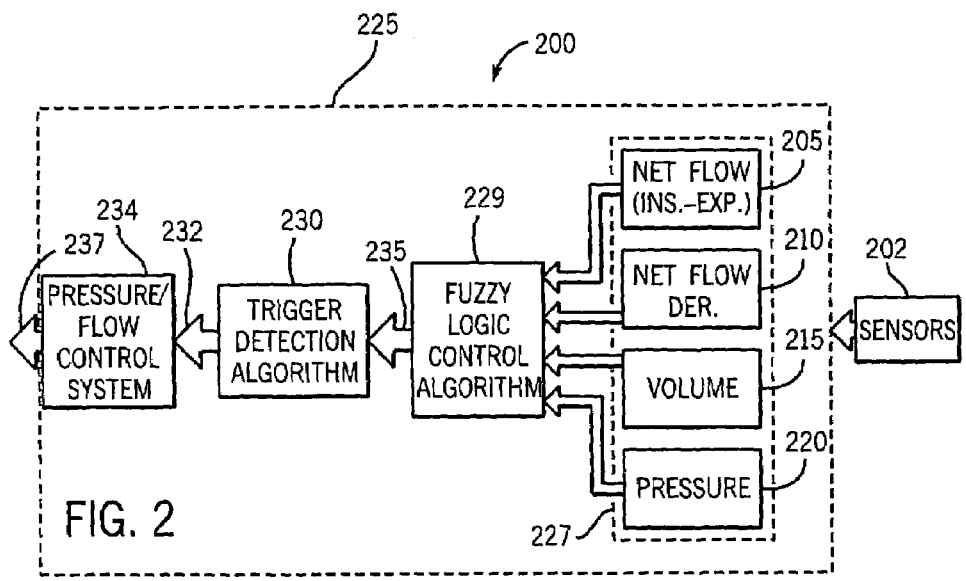
FIG. 2 illustrates a block diagram representation of the system according to an embodiment of the present invention.

FIG. 2 depicts a block diagram of the trigger adjustment system 200 of the present invention. In this trigger adjustment system 200, a net flow component 205, a net flow derivative component 210 and a volume component 215 are all calculated by signal process. Algorithm 227, using patient inputs which are detected by sensors 202 and sent to a processor 225 where the patient inputs are calculated into the components 205, 210, 215. A pressure input 220 is also received by the sensors 202 and sent to the processor 225. The fuzzy logic control algorithm 229 in the processor 225 calculates an appropriate trigger threshold level using these inputs, and sends this most sensitive trigger reference signal 235, to a trigger detection algorithm 230 that detects patient triggers. This algorithm causes a ventilator control to start an inspiratory phase for the patient by sending a notification signal 232 to the pressure/flow control system 234. The trigger adjustment system 200 of the present invention continuously receives the net flow input 205, the net flow derivative input 210, the volume input 215 and the pressure input 220, thus allowing the control algorithm 229 to continuously calculate the proper trigger threshold level. The control algorithm 229 continuously outputs a new trigger threshold signal 235 to the trigger detection algorithm 230 which receives the adjusted trigger threshold level. The trigger detection algorithm 230 and the pressure/flow control system 234 calculate the appropriate manifold signal 237 as well as further specifics of the architecture of the trigger adjustment system 200 will be discussed in greater detail below.

Figure 3:
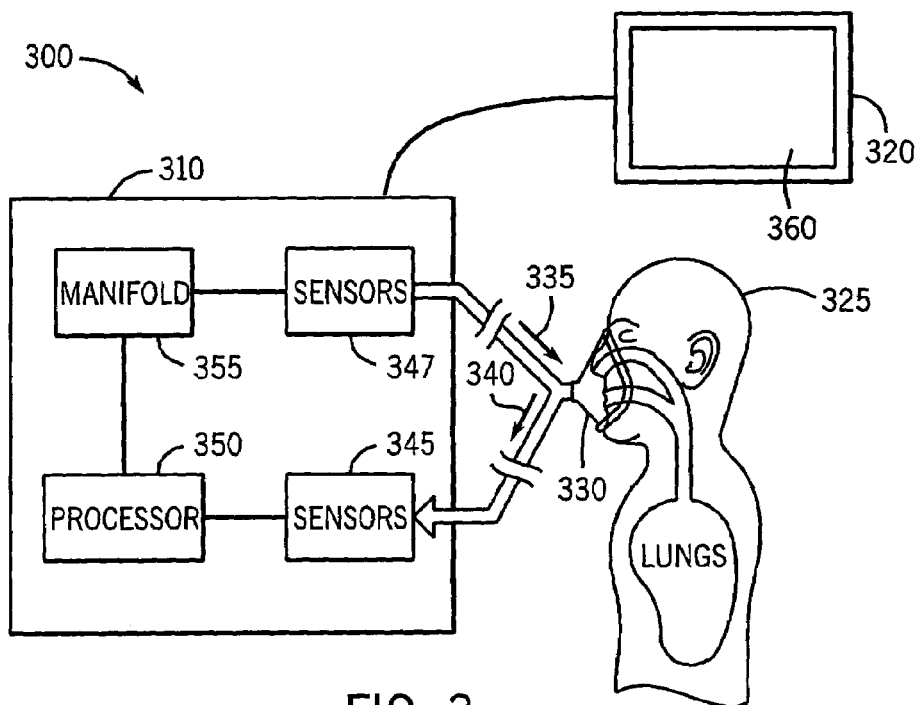
FIG. 3 illustrates a schematic representation of the system according to an embodiment of the present invention.

Referring now to FIG. 3, the trigger adjustment system 300 of the present invention is illustrated. In this schematic representation, the patient 325 wears a mask 330, the mask 330 being connected to the ventilator 310 with an inspiratory tube 335 and an expiratory tube 340. Gas travels out of the manifold 355, past the sensors 347, through the inspiratory tube 335, and then the expiratory tube 340 is received by additional sensors 345 and 347 in the ventilator 310. The sensors 345 and 347 detect the various input levels as described and shown in FIG. 2, including the patient inputs that are processed and used to calculate the net flow component 205, the net flow derivative component 210, the volume component 215. The pressure input 220 is also detected. The sensors 345 and 347, after detecting these inputs, provide the inputs to the processor 350. The adaptive trigger threshold algorithm running on the processor 350 receives these inputs and calculates the trigger threshold. This new trigger threshold value (or trigger reference signal) is sent to the breath detection algorithm, and this algorithm upon detection of triggers notifying the pressure/flow control system that provides a control signal (not shown) to the manifold 355, the manifold including the controller 230 (FIG. 2). The manifold 335 then adjusts the gas provided to the patient 325 through the inspiratory tube 335 and mask 330, according to the adjusted trigger threshold level.

Still referring to FIG. 3, the trigger adjustment system 300 of the present invention also includes a display 320 having a graphical user interface 360. The display 320 and the graphical user interface 360 allows a user of the trigger adjustment system 300 such as a physician, to monitor the patient's progress and also to adjust the treatment of the patient 325.

The operation of the trigger adjustment system 300 as depicted in FIG. 3 is predicated on the trigger menu option being set to "auto".

Figure 4:
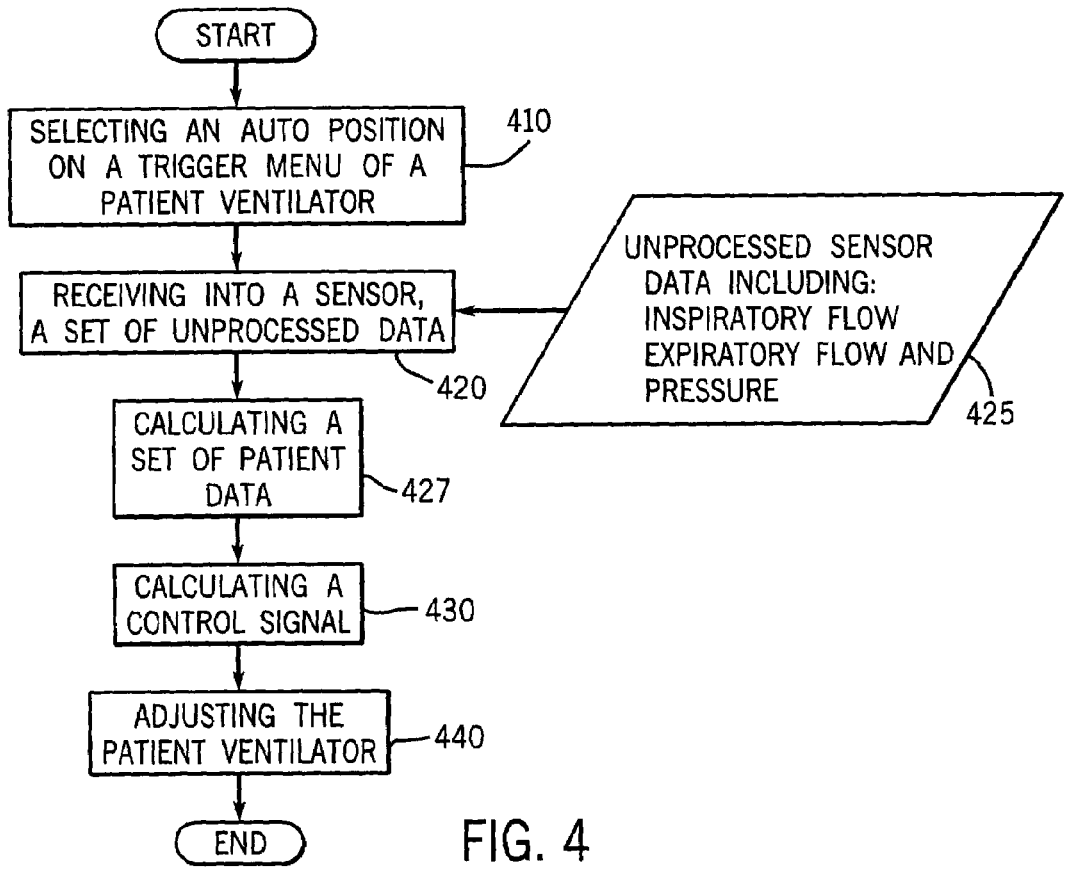
FIG. 4 illustrates a flow chart representation of the method according to an embodiment of the present invention.

FIG. 4 depicts the method of adjusting the trigger of the preferred embodiment of the present invention. In step 410, an auto position on a trigger menu of a patient ventilator is selected. In step 420, a set of unprocessed data is received into a sensor. The set of unprocessed data 425 includes inspiratory flow, expiratory flow and pressure. In step 427, a set of patient data is calculated with the set of unprocessed data. In step 430, a control signal is calculated as described above. Finally, in step 440, the patient ventilator is adjusted according to the set of patient data from step 427.

Once a steady state is reached where the false triggers 120, 130 are no longer occurring, or rarely occurring, the trigger threshold will not be raised further. In addition, the amount of adaptive adjustment can be limited to a specified band and can be specified by the user. In the event these false triggers 120, 130 (FIG. 1) are not occurring over a given time period, the algorithm can lower the trigger threshold (sensitize) until they occur only occasionally again. This will repeat many times over the course of an hour as a method of verification within the algorithm that the threshold is the most sensitive possible while still filtering out false triggers.

The system of the present invention will also have the capability to adjust the trigger level in finer increments than what is available on the user interface, if a clinician were to make the adjustment manually.

In operation, in the present invention, under the trigger menu option, "auto" can be selected. When "auto" is selected, a software algorithm (as will be described later in detail) using signal processing techniques will detect what the appropriate trigger time-frame, the ratio of tidal volumes between triggers, flow acceleration comparisons, inspiratory and expiratory phase timing to raise the trigger threshold. To lower the trigger threshold the algorithm will take into account the complete absence of false triggers over a time window as well as increases in average flow and or pressure differential, or even pressure drop in general over a time window. The algorithm will use this data to "learn" the characteristics of how the patient is initiating his or her breaths and triggering the ventilator.

The system and method of the present invention eliminates the time spent by the clinician to adjust the trigger level when the patient is first breathing on the ventilator, as well as time spent periodically changing the setting due to changing lung or system conditions. The adaptive control algorithm on the trigger sensitivity can make very small adjustments for each control loop update. In contrast, the typically large increments that are allowed for manual trigger threshold adjustment on the user interface.

The system and method of the present invention adaptively adjusts the trigger threshold sensitivity of a ventilator. This adaptive adjustment is preferably achieved by implementing an algorithm that makes use of several signals to detect these conditions: commanded flow output from the ventilator control system into the breathing circuit (q*), net commanded flow ($q^*_{net}$) going into the patients' lungs, acceleration of measured net flow ($q^*_{net}$), and net Volume over the course of a breath. In addition, measured values used to help calculate the above are as follows: Inspiratory flow ($q_{inspiratory}$) and expiratory flow ($q_{expiratory}$) are the measured flows going toward and away from a patient, respectively, as detected by flow transducers.

Commanded net flow, or $q^*_{net}$ is calculated as follows:

$$q^*_{net} = q^* - q_{expiratory}$$

The equivalent of net flow acceleration, $q^*_{net}$ can be represented in recursive form as follows:

$$q^*_{net}(k) = T[q^*_{net}(k) - q^*_{net}(k-1)],$$

where T is the sample period. Running Volume over the course of a breath can be calculated using time weighted accumulation of flow, wherein $t_1$=breath start time, and $t_2$=breath end time:

$$\text{Volume} = \sum_{t_1}^{t_2} Tq*\text{net}.$$

In the preferred embodiment, the first automatic adjustment to flow trigger threshold level will be to correct for leak. One method for leak level detection is discussed in Jafari (column 8, lines 15-40). The flow trigger threshold level will then be automatically adjusted for offset in flow valve calibration. When the flow command is "stable" for a given time, a snapshot of the average $q^*$ over that time window, as well as a snapshot of the average $q_{inspiratory}$ can be taken. The error between the $q^*$ and $q_{inspiratory}$ can be applied to adjust the flow trigger threshold. Third, in the chance that a stable flow is not reached, a snapshot of $q^*_{net}$ can also be obtained at the time that the trigger conditions are met. If negligible flow acceleration was observed within a small time window of the trigger occurring, it can be assumed that this trigger was automatic. When this is the case, the flow trigger value can be desensitized incrementally or by a gain factor multiplied by the error. The algorithm will also have the capability to adjust the trigger level in finer increments than what is available on the user interface. This process will be repeated for each breath to maintain the most sensitive and most practical flow trigger threshold possible.

The present invention has been described in terms of specific embodiments incorporating details to facilitate the understanding of the principles of construction operation of the invention. Such reference herein to specific embodiments and details thereof is not intended to limit the scope of the claims appended hereto. It will be apparent to those skilled in the art of modifications maybe made in the embodiment chosen for illustration with departing from the spirit and scope of the invention.

What is claimed is:

1. A method of adjusting an inspiratory trigger threshold level of a patient ventilator having a trigger menu, the method comprising: manually selecting an auto position on the trigger menu of the patient ventilator; receiving into a processor of the patient ventilator a set of detected data from a flow sensor and a pressure sensor, wherein the set of detected data includes an inspiratory flow component, an expiratory flow component, and a pressure component; calculating a set of patient data in the processor with the set of detected data, wherein the set of patient data includes a net flow component, a net flow derivative, a volume component and the pressure component; using a fuzzy logic control algorithm to calculate a control signal with the set of patient data in the processor, wherein the control signal corresponds to an adjusted inspiratory trigger threshold level; and sending the control signal to a controller of the patient ventilator such that the controller adjusts the inspiratory trigger threshold level of the patient ventilator to reflect the adjusted inspiratory trigger threshold level, wherein the inspiratory trigger threshold level is adjusted according to the method to prevent false triggers.

2. The method as claimed in claim 1, wherein the set of patient data is calculated with a signal processing algorithm in the processor and the control signal is calculated with the fuzzy logic control algorithm, and further wherein the fuzzy logic control algorithm is used by the processor to execute the adjustment of the inspiratory trigger threshold level.

3. The method of claim 1, further comprising displaying the set of patient data on a display device coupled to the patient ventilator.

4. The method as claimed in claim 1, further comprising limiting an adaptive inspiratory trigger adjustment amount to a band specified by a user.

5. A system for adjusting an inspiratory trigger threshold level of a patient ventilator, the system comprising: a trigger menu of the patient ventilator, wherein the trigger menu is set to an auto position manually; a flow sensor and a pressure sensor configured to collect a set of detected data, wherein the detected data includes an inspiratory flow component, an expiratory flow component, and a pressure component; a processor, coupled to the sensor, wherein the processor receives the detected data and calculates a set of patient data with the set of detected data, wherein the patient data includes a net flow component, a net flow derivative, a volume component and the pressure component, and further uses a fuzzy logic control algorithm to calculate a control signal with the set of patient data, and further wherein the control signal corresponds to an adjusted inspiratory trigger threshold level; and a controller coupled to the processor and configured to receive the control signal, wherein the controller adjusts the inspiratory trigger threshold level of the patient ventilator to reflect the adjusted inspiratory trigger threshold level, wherein the inspiratory trigger threshold level is adjusted to prevent false triggers.

6. The system as claimed in claim 5, further comprising a display coupled to the patient ventilator, wherein the display is configured to display the set of detected data and the set of patient data.

7. The system as claimed in claim 5, wherein the processor applies an algorithm to calculate the control signal.

8. A method of adjusting an inspiratory trigger threshold of a patient ventilator having a trigger menu, the method comprising: manually selecting an auto position on a the trigger menu of the patient ventilator; receiving into a processor of the patient ventilator a set of detected data from a flow sensor and a pressure sensor, wherein the set of detected data includes an inspiratory flow component, an expiratory flow component, and a pressure component; calculating a set of patient data in the processor with the set of detected data, wherein the set of patient data includes a net flow component, a net flow derivative, a volume component and the pressure component; using a fuzzy logic control algorithm to calculate a control signal with the set of patient data in the processor, wherein the control signal corresponds to an adjusted inspiratory trigger threshold level; sending the control signal from the processor to a controller; adjusting the inspiratory trigger threshold level of the patient ventilator with the controller to the adjusted inspiratory trigger threshold level, wherein the inspiratory trigger threshold level is adjusted according to the method to prevent false triggers; and displaying the set of patient data and the set of detected data on a device coupled to the patient ventilator.

* * * * *